US00PP20889P3

(12) United States Plant Patent
Dressel

(10) Patent No.: US PP20,889 P3
(45) Date of Patent: Mar. 30, 2010

(54) GRAPEVINE PLANT NAMED 'ZINTHIANA'

(50) Latin Name: *Vitis vinifera*
Varietal Denomination: Zinthiana

(76) Inventor: Lucian W. Dressel, RR 2, Suite 207, Carrollton, IL (US) 62016

( * ) Notice: Subject to any disclaimer, the term of this patent is extended or adjusted under 35 U.S.C. 154(b) by 0 days.

(21) Appl. No.: 11/978,489

(22) Filed: Oct. 30, 2007

(65) Prior Publication Data

US 2009/0113575 P1 Apr. 30, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent L Bell

(57) ABSTRACT

A new and distinct, self rooted, variety of grapevine plant, 'Zinthiana', from a cross of 'Zinfandel' and 'Cynthiana', which can be distinguished by its outstanding wine combined with high productivity, disease resistance, and cold hardiness superior to one of its two acclaimed parents 'Zinfandel'.

4 Drawing Sheets

Botanical classification: *Vitis vinifera* 'Zinfandel' crossed with 'Norton'.

Varietal denomination: 'Zinthiana'.

BACKGROUND OF THE INVENTION

Most grape varieties used for production of high quality wines around the world are of the species *Vitis vinifera.* These *V. vinifera* varieties, when cultivated in northern regions of the United States with a continental climate are often subject to serious injury or death from low temperatures during winter. *V. vinifera* must also be grafted onto an American rootstock in order to be grown successfully. Although several wild *Vitis* species occur in colder regions of North America and eastern Asia, the wine made from these species generally has serious defects. Thus, a great need existed for grape plants that would combine the superior wine quality of *V. vinifera* with the cold weather resistance and disease resistance of wild species yet be free of their unpleasant wild flavors. A grape breeding program conducted by Lucian W. Dressel at Davis, Calif. and at Winters, Calif. from 2000 to 2002 developed such varieties by combining various *V. vinifera* with the native grape plant known as 'Norton' (aka 'Cynthiana').

BRIEF SUMMARY OF THE INVENTION

The invention is a new and distinct variety of grape plant designated 'Zinthiana' which produces dark black fruit highly suitable for red wine production, and has a combination of high wine quality, excellent cold hardiness, disease resistance, good productivity, and does not need to be grafted. It has proven to be well adapted to various states including California, Missouri, Illinois, Kentucky, Louisiana and Iowa. 'Zinthiana' resulted from a cross of 'Zinfandel' and 'Norton' made in 2001 in Winters, Calif.

'Zinthiana 'propagates well from hardwood cuttings. Once rooted the young plants quickly become established, and all 'Zinthiana' plants propagated in this manner have been genetically stable, producing only dark black fruit with dark reddish bluish juice. The vines of 'Zinthiana' have an abundance of tendrils and easily adapt themselves to a high wire cordon trellis system. Canes have a drooping growth attitude and are easily combed and trained. The bud break and bloom of 'Zinthiana' are very late, typically after that of both 'Zinfandel' and 'Norton'. Its flowers are perfect and self fertile. 'Zinthiana' vines typically set a moderate to heavy crop. The fruit of 'Zinthiana' is borne on long clusters that are tight, compact and often ave a small wing when mature. The peduncles are 'Norton'-like being very long. The berries are medium in size with a waxy bloom at maturity. Berry splitting and bunch rot have not been observed to date, nor has crown gall. In commercial vineyards on a normal spray schedule no disease problems have been noted from Black Rot, Downey Mildew, Powdery Mildew, or any other fungus disease or insects. Resistance to Pierce's Disease is unknown, but is being tested in Louisiana.

The fruit of 'Zinthiana' can be fermented to produce a dry red wine that can be barrel aged to produce a wine in the classic style of a red California 'Zinfandel'. The wine has none of the flavors associated with wines made from either French Hybrid grapes or *V. Labrusca* varieties. 'Zinthiana's' wine is bright crimson, like dark red rose pedals. The nose is peppery, with currents, some cedar, complex, not grapey, hint of figs. Taste is a more complex version of 'Zinfandel', delightful, charming.

'Zinthiana' is much more cold hardy than its parent 'Zinfandel' and has the advantage of being self rooted so that even if the plant is killed to the ground it can be renewed from an underground sucker, unlike 'Zinfandel'. Unlike its other parent, 'Norton', its growth habits are quite orderly and manageable and 'Zinthiana' does not have to be grown on a double curtain system to be profitable.

BRIEF DESCRIPTION OF THE FIGURES

FIG. 1—'Zinthiana' Leaf—A photograph showing the front view of a 'Zinthiana' leaf.

FIG. 2—'Zinthiana' Leaf—A photograph showing the rear view of a 'Zinthiana' leaf.

FIG. 3—'Zinthiana' Vine—A photograph showing trunk, canes, leaves and fruit after verasion in 2006.

FIG. 4—'Zinthiana' Bunches—A photograph of 'Zinthiana' showing a close up of three typical fruit cluster after verasion, Aug. 31, 2006.

The colors in the photographs are as close as possible with the photographic and printing technology utilized. The color values cited in the detailed botanical description accurately describe the colors of the new grape.

DETAILED BOTANICAL DESCRIPTION OF THE INVENTION

The following descriptions of 'Zinthiana' apply to vines planted in Carrollton, Ill. in 2004. When dimensions, sizes, colors and other characteristics are given, it is to be understood that such characteristics and approximations set forth as accurately as possible. Variations of the usual magnitude incident to climatic factors, fertilization, pruning, pest control and other cultural practices are to be expected.

The colors referred to in this abstract are those of The Royal Horticultural Society Colour Chart, copyrighted 2005

VINE

General:

*Size.*—The test grapevines of 'Zinthiana' are planted approximately 8 feet apart down the row and 10 feet apart between the rows. The vine canopy extends from 0.75 meters to 1.0 meters out in to the row. The vines are in their fourth leaf.

*Vigor.*—When first planted, much more vigorous than 'Norton'. When mature equally vigorous as 'Zinfandel' but without the rampant and unruly growth habits of 'Norton'.

*Productivity.*—Productive, bearing 4 tons to 6 tons per acre depending on pruning and growing conditions.

Trunk:

*Surface texture.*—Rough textured and furrowed and only slightly shaggy.

*Bark color.*—Brownish. Varies from 200A to 202A.

*Trunk circumference.*—Very straight, round, and uniform in diameter ranging from 3.6 cm to 3.8 cm at 40 cm height from ground to 3.6 cm to 3.8 cm at 600 cm from the ground.

MATURE CANES

Size:

*Thickness.*—Canes that arise from dormant spurs vary from 6 mm to 14 mm at 5 cm to 40 cm from bud. Canes are relatively uniform in width, like 'Norton' and do not taper like 'Vidal'.

Surface: Smooth often finely striated.

Color: Canes are reddish brown on top (45A) and light green underneath (145A).

Internode length: Varies widely depending on type of arm, position on vine and the nature of the bud from which each cane arose. From 3 cm to 4 cm on smaller shorter arms and laterals and from 10 cm to 15 on larger canes. Varies from 9 to 14 cm on the stronger upper suncanes and from 3 to 5 cm on lateral canes.

TENDRILS

Relatively long ranging from 14 cm to 30 cm.

Diameter: Varies from 1.0 to 2.0 mm in thickness measured at the base of the tendril.

Distribution: Discontinuous.

Form: Predominately bifid, although trifid tendrils may be present.

Color: Reddish brown (45A).

GROWING TIPS

Straight, and uniformly green (137C)

LEAVES

Mature leaves:

*General.*—Like its parent 'Norton', the leaves of 'Zinthiana' can have a wide variety of shapes and sizes on the same plant. Variations can be caused by the age of the vine, the location where grown, the weather and any number of other factors.

*Average leaf length.*—17 cm measured from the apex of the central lobe to the bottom of the petiole junction.

*Average leaf width.*—16 cm measured at a center of leaf, 8.5 cm from apex and at a 45 degree angle to central vein.

*Apex of leaf.*—Length of apex 6 cm; width of apex 6 cm. Long pointed tooth on top of apex averaging 1 cm in length. Remaining teeth on apex are small, 1 mm, or non-existent.

*Base of leaf.*—Rounded, gradually sloping upwards, approximately 14 cm wide. General shape of petiole sinus; Long 5 cm on average mature leaf, narrow 8 mm, slightly bulb-like in middle 1 cm wide on average widening into a V shape 5 cm in length.

*Shape of upper leaf sinus.*—Generally in a long narrow V shape.

*Leaf margins.*—Dentate with irregular teeth, commonly approximately 10 teeth to 12 teeth per lobe, and approximately 50 teeth to 60 teeth on entire leaf.

*Average blade length.*—17 cm as measured from the apex of the center leaf lobe to the petiole junction.

*Average blade width.*—16 cm on average for a mature leaf.

*Size of blade.*—Large, usually having 5 lobes.

*Shape.*—Orbicular. Galet coordinates: 015-2-37.

Shape of teeth along leaf margins: Convex.

Length of teeth along leaf margins: Medium to large and variable, 6 mm to 14 mm in length.

General shape of petiole sinus: Long, narrow, slightly bulb like in middle widening into a V shape.

Shape of upper leaf sinus: Generally in a long narrow V shape.

Leaf color:

*Upper leaf surface.*—Glabrous, rough (137C).

*Lower leaf surface.*—Rather dull and lighter in intensity of color (137C).

*Upper leaf veins.*—Yellowish-green (2C) with a blush of red color on the five main veins (44A) from the petiole junction to the first main vein.

*Lower leaf veins.*—The color of the five main veins from the petiole sinus to the first branching vein is distinctly red (44A), beyond which they are yellow-green (2C).

Surface texture: Rough, glabrous.

Surface appearance: Dull.

Lower surface texture: Rough, dull.

Leaf petiole:

*Length of petiole.*—7 cm.

*Petiole thickness.*—3.0 mm to 4.0 mm measured at mid petiole.

*Petiole shape.*—glabrous, smooth.

*Petiole color.*—Reddish-brown (172A)

*Length of petiole compared to mid vein.*—about 60%.

FLORAL CLUSTER DESCRIPTION:

Bloom timing: Varies widely from year to year. Generally late, slightly after 'Norton'. May 10$^{th}$ in 2006.
Cluster form: Long narrow.
Clusters per shoot: Usually three.
Floral cluster length: Average 110 cm.
Floral cluster width: Average 30 cm.
Cluster peduncles: Length 10 cm to 12 cm, thickness 3.0 mm to 4.0 mm
Peduncel color: Green (145A)
Inflorescence: Hermaphroditic.
Floral stamens: Upright with normal size anthers
Flower length: 2 mm in average flower
Flower diameter: 1 mm in average flower
Flower petals: Five in number, and open from the bottom to the top. Remaining entire after separaton. Petals ovoid in shape with 5 sections remaining attached to one another after falling to ground, 3 mm in diameter. Apex of petals is concave with reddish dot in center of petal clusters (41A). Base is smooth and 2.5 gm in circumference. Margins are smooth and convexly curved. Color on top surface of petals is grass green (145C). Color on underside of petals is light green (149D).
Sepals:—Five in number, and commonly very poorly developed or nonexistent. If present, appearing as little more than a dusty residue with a light green color (149D).
Pollen amount: Abundant.
Pollen color: Pale yellow (27D).
Calyptras separation from the flower base: Complete
Duration of bloom: Average 10 days to 12 days depending on ambient temperatures during the bloom period.

FRUIT DESCRIPTION—PRIMARY CLUSTERS

Date of maturity: Sep. 20, 2006 in west central Illinois.
Bunch size: Long, medium.
Bunch length: 12 cm to 25 cm, not including the peduncle.
Bunch width:15 cm to 25 cm.
Bunch form: Conical.
Bunch weight: Average from 200 gm to 300 gm.
Bunch density: Tight like 'Norton'.
Peduncle length: Long like 'Norton' from 5 cm to 8 cm.
Peduncle color: Green when growing (152D), brown (22C) when mature.
Peduncle thickness: Ranges from 3.0 cm to 5.0 cm at the peduncle base.
Berry form: Round.
Cross sectional view berry form: Globose.
Berry size: Medium 12 mm to 15 mm in diameter.
Berry weight: 2 gm to 5 gm
Berry uniformity: Excellent.
Berry pedicle: Small to medium size.
Berry pedicle length: 5 mm to 6 mm
Berry pedicle thickness: 1 mm to 2 mm
Attachment: Very strong with no shatter at commercial maturity.
Berry skin color: Black with waxy bloom. 100% colored.
Berry skin thickness: Medium.
Berry skin surface texture: Smooth and glabrous.
Berry skin, tenacity to flesh: Skin is tenacious to the flesh.
Berry skin, tendency to crack: Has never shown any cracking.
Berry skin, reticulation: Surface is smooth with no reticulations present.
Berry color: Black (202A)
Berry surfaces: Uniformly covered with a waxy, grayish (192B) bloom.
Berry flesh color: Light translucent green (145C)
Juiciness of flesh: Similar to standard commercial wine varieties. Much juicier than 'Norton', not as juicy as 'Zinfandel'.
Berry firmness: Very firm.
Berry juice: Clear, light yellow (4D) and slightly pinkish (38D) at crushing.
Solids-sugar percentage (at maturity): 22.0 on Sep. 12, 2006
pH of berry juice: 3.18 on Sep. 12, 2006
Titratable acidity: 7.75 gm/liter
Seed: Viable, 3 seeds per berry to 4 seeds per berry, average size and shape for *V. vinifera*
Flavor: Good, tart, sweet, typical *V. vinifera* red wine grape flavor
Aroma: Typical crushed red wine grape aroma. No wild aromas.

SECONDARY BUNCHES

Almost no secondary bunches have been observed in normal years with no spring frost.

COMPARISON BETWEEN PARENTAL AND COMMERCIAL CULTIVARS

The physical appearance of the vine of 'Zinthiana ' more closely resembles that of its parent 'Zinfandel'. Like 'Zinfandel' the leaves of 'Zinthiana' are more modest in size and show fewer variations than do the leaves of its parent 'Norton'. The growth habits are more orderly than 'Norton' and it can produce normal crops of between 4 tons to 6 tons per acre without having to be grown on a double curtain trellis system. 'Zinthiana' is far more resistant to the endemic vine diseases of the eastern US than 'Zinfandel' and it can be grown on its own roots.

The berries and bunches are much larger than 'Norton' and the berries have fewer seeds making wine making easier.

The invention claimed is:

1. The new and distinct variety of Grapevine Plant as illustrated and described.

* * * * *

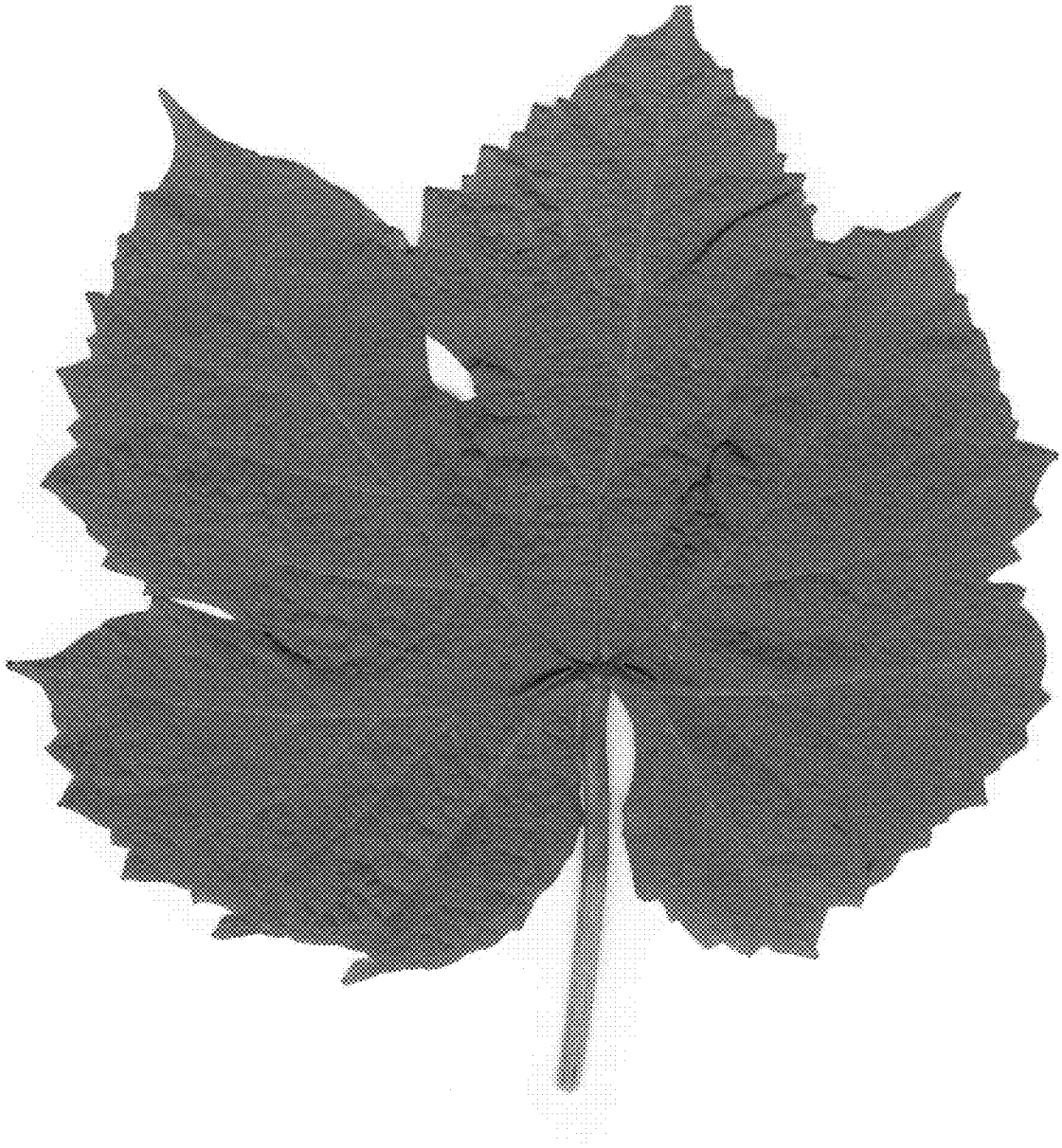

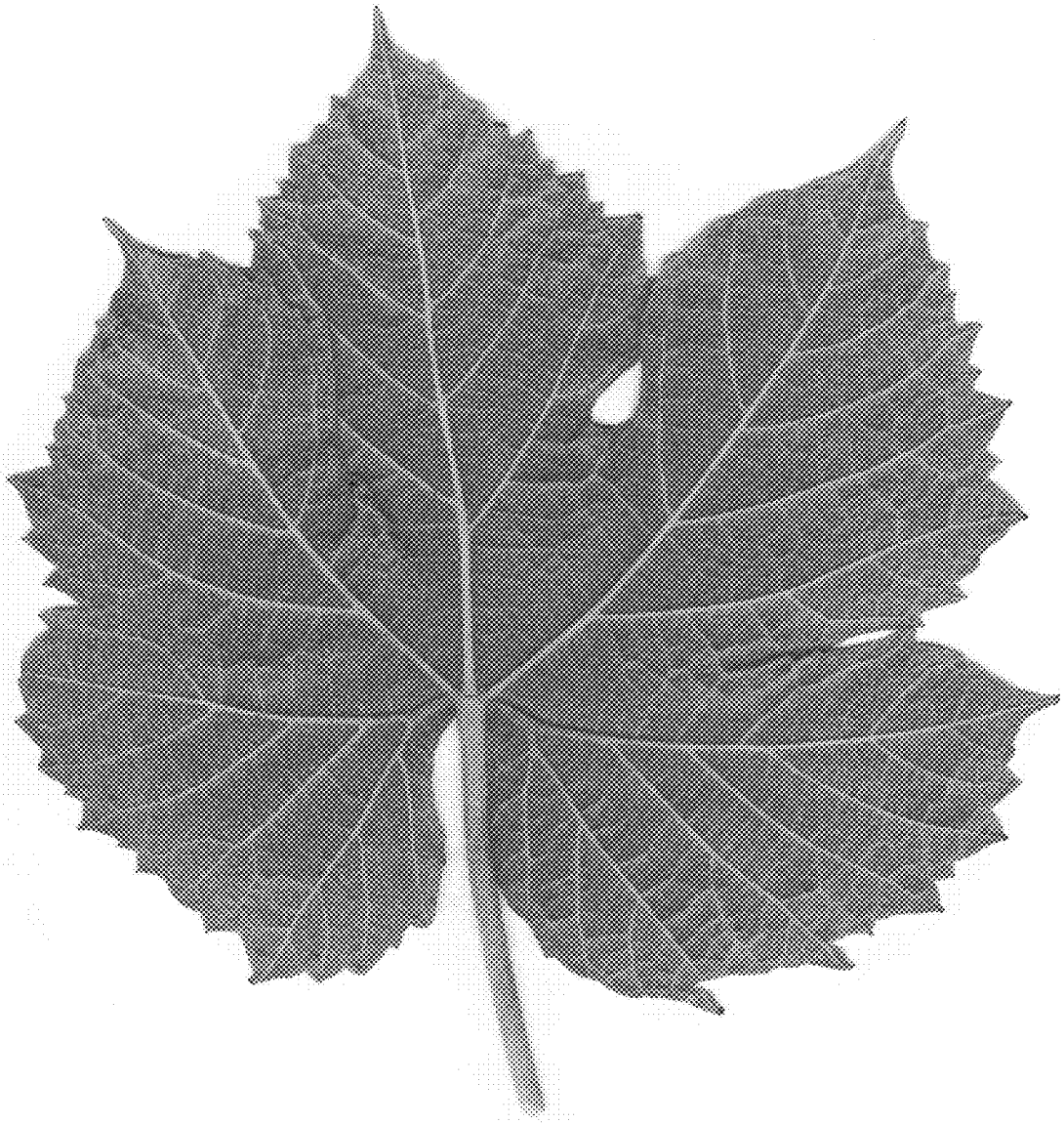

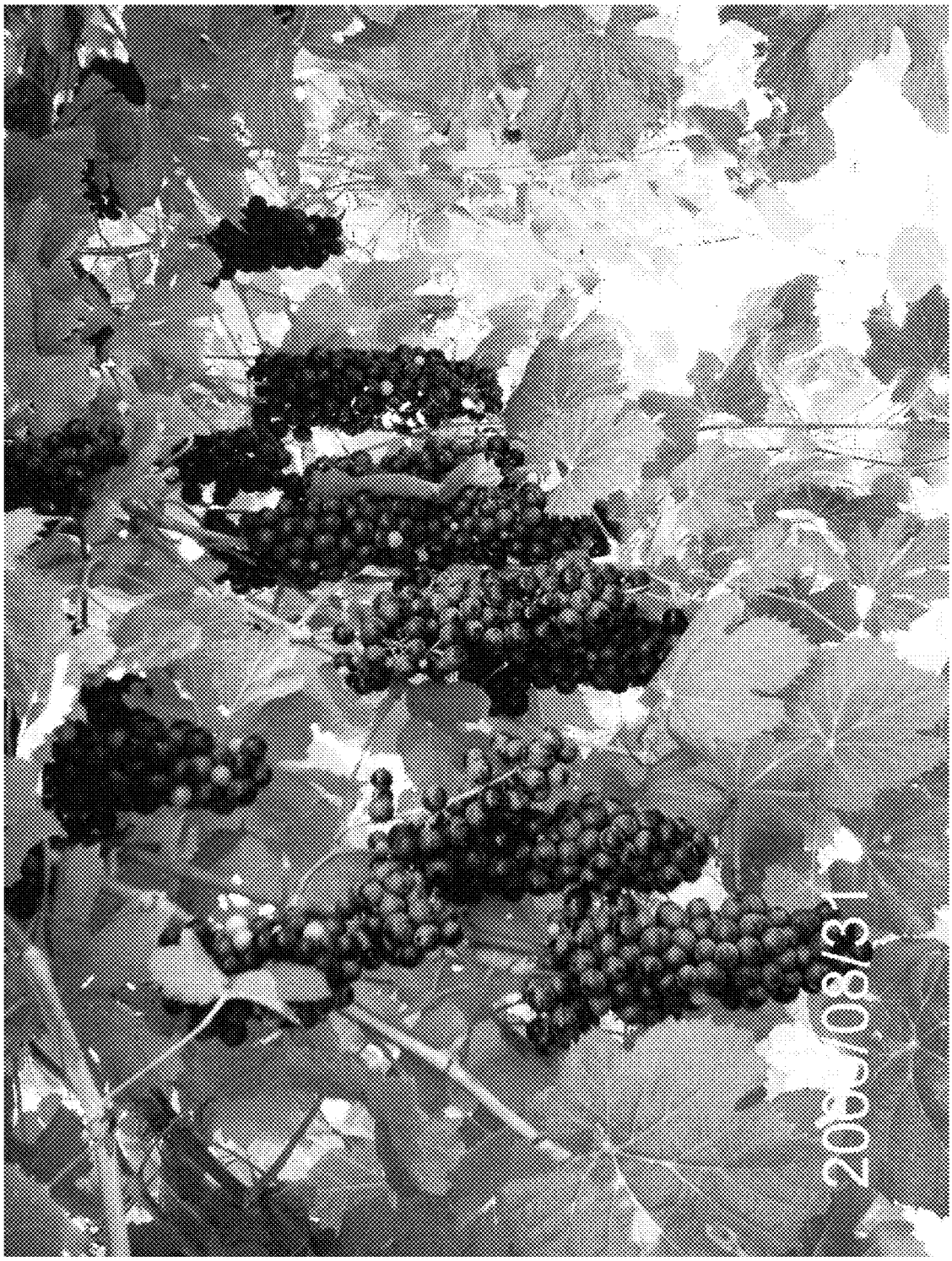
2008/08/31

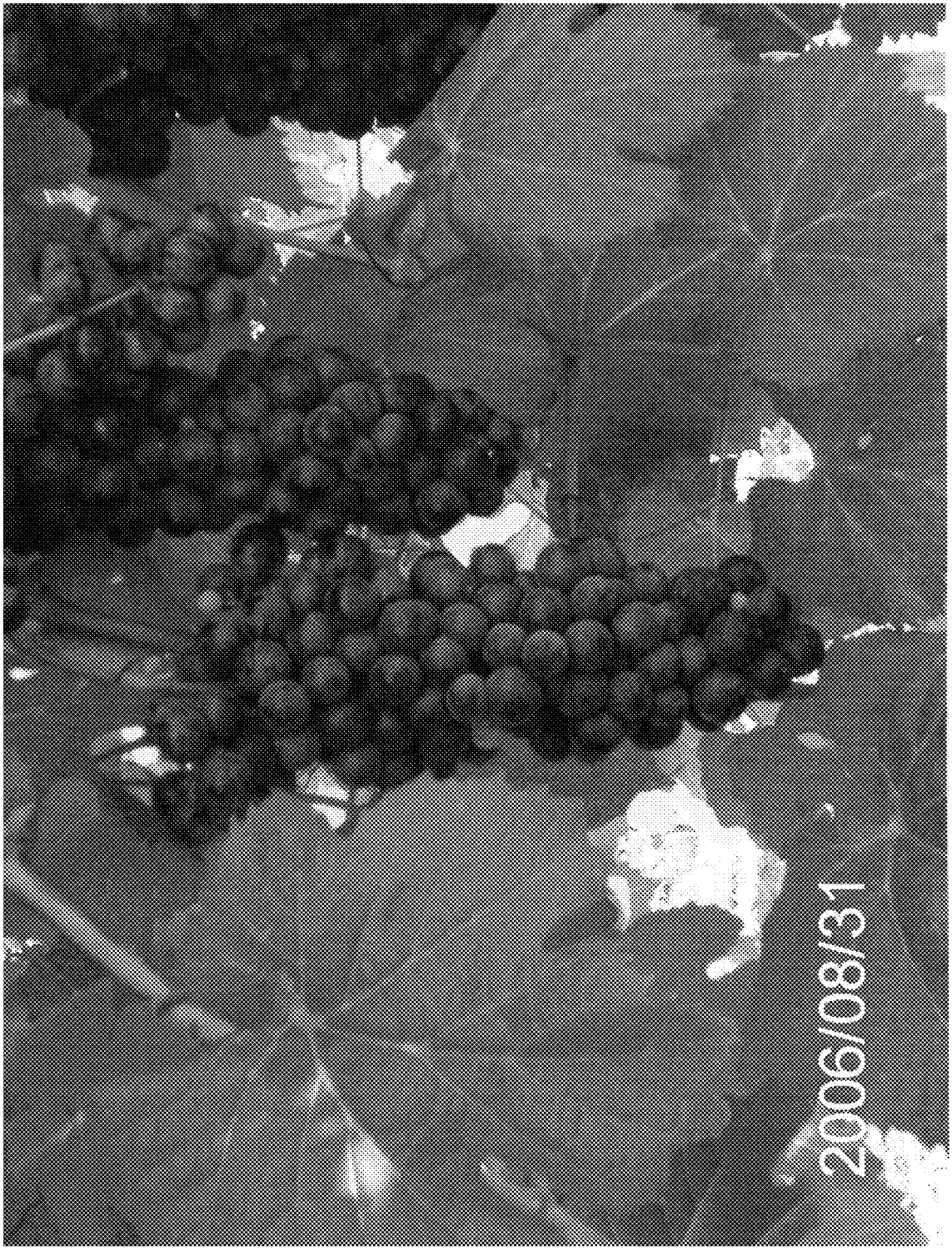
2006/08/31